(12) United States Patent  
He

(10) Patent No.: US 7,885,383 B1
(45) Date of Patent: Feb. 8, 2011

(54) METHOD FOR MEASURING CRYSTALLITE SIZE WITH A TWO-DIMENSIONAL X-RAY DIFFRACTOMETER

(75) Inventor: Bob B. He, Madison, WI (US)

(73) Assignee: Bruker AXS, Inc, Madison, WI (US)

( * ) Notice: Subject to any disclaimer, the term of this patent is extended or adjusted under 35 U.S.C. 154(b) by 59 days.

(21) Appl. No.: 12/477,615

(22) Filed: Jun. 3, 2009

(51) Int. Cl.
*G01N 23/207* (2006.01)
*G01N 23/20* (2006.01)

(52) U.S. Cl. .......................................... 378/73; 378/71
(58) Field of Classification Search ................... 378/70, 378/71, 73, 83, 86
See application file for complete search history.

(56) References Cited

U.S. PATENT DOCUMENTS 6,064,717 A * 5/2000 Ortega et al. ................... 378/71
6,882,739 B2 * 4/2005 Kurtz et al. ................. 382/109
7,236,566 B2 * 6/2007 Gibson et al. ................. 378/71
7,620,148 B2 * 11/2009 Harel et al. ................... 378/70

* cited by examiner

*Primary Examiner*—Irakli Kiknadze
(74) *Attorney, Agent, or Firm*—Law Offices of Paul E Kudirka

(57) ABSTRACT

Crystallite size in a sample is determined by performing a quantitative γ-profile analysis on a diffraction ring in a two-dimensional X-ray diffraction pattern. In particular, a two-dimensional X-ray diffraction system is first calibrated with a sample having a known crystallite size, crystal structure and X-ray absorption coefficient. For a given instrument window, the number of grains contributing to a selected diffraction ring is determined by the effective diffraction volume, grain size and the multiplicity of the diffracting crystal planes. The grain size of an unknown sample can then be determined by a quantitative analysis of the diffraction ring.

20 Claims, 3 Drawing Sheets

METHOD FOR MEASURING CRYSTALLITE SIZE WITH A TWO-DIMENSIONAL X-RAY DIFFRACTOMETER

BACKGROUND

The properties of polycrystalline materials are determined by the properties of the crystallites that form the material and the boundaries between the crystallites. Crystallites may also be referred to as grains, particles or simply crystals. The size of the crystallites in a polycrystalline material has significant effects on many of its properties, such as thermal, mechanical, electrical, magnetic and chemical properties. For instance, the mechanical strength of polycrystalline metals and alloys is strongly dependent on the grain size. This is, in part, due to the fact that deformation of metals is caused by the motion of dislocations and other defects under loading stress and different crystallographic orientations and the boundaries between adjacent grains serve as barriers to the motion of such dislocations and other defects. A metal with finer grains has more boundaries to impede dislocation motion and, therefore, has higher mechanical strength. Particle size can also affect the behavior of pharmaceuticals in many ways, such as dissolubility, bioactivity, flow properties and stability.

Consequently, it is important to measure crystallite size in order to determine or predict the properties of a polycrystalline material. Crystallite size can be measured by many techniques, such as by optical microscopy or electron microscopy techniques on polished and etched surfaces. However, both microscopy techniques require special sample preparation and can only observe the sample surface. X-ray diffraction has been used for crystallite size measurement for over ninety years since X-rays can penetrate a sample and measure crystallite size over the entire volume of the sample, thereby allowing the overall statistics of the crystallite size to be calculated.

The conventional method for determining particle size with X-ray diffraction measurements is based on diffraction peak broadening or diffraction (2θ) profile analysis. When crystallites in a sample are less than approximately 100 nm in size, appreciable broadening in the x-ray diffraction lines measured from that sample will occur and can be used to estimate the average crystallite size. Where the crystallites are stress-free, the size can be estimated from a single diffraction peak; however, where stress may be present, several diffraction peaks may have to be analyzed. The extent of the broadening is described by the measured value B, which is the full width at half maximum intensity of the peak.

After the value of B (in radians) is corrected for instrumental contribution to the broadening, it can be substituted into Scherer's equation for the particle size D:

$$D \approx \frac{0.9\lambda}{B\cos\Theta}$$

where $\lambda$ is the X-ray wavelength and $\Theta$ is the diffraction angle.

Although X-ray diffraction line broadening is clearly present when the particle size is smaller than 100 nm, in practice, the Scherer equation can adequately determine the average size of crystallites smaller than 30 nm when the broadening is significant enough to be resolved from instrumental broadening. However, there are many situations where it would be desirable to measure particle size where the particle size is considerably larger than 100 nm. For instance, the particle sizes in pharmaceutical systems are typically in the range of a few micrometers to millimeters. In these systems, conventional methods of particle size analysis by x-ray diffraction are not always suitable.

SUMMARY

In accordance with the principles of the invention, crystallite size is determined by performing a quantitative γ-profile analysis on a diffraction ring in a two-dimensional X-ray diffraction pattern. In particular, a two-dimensional X-ray diffraction system is first calibrated with a sample having a known crystallite size, crystal structure and X-ray absorption coefficient. For a given instrument window, the number of grains contributing to a selected diffraction ring is determined by the effective diffraction volume, grain size and the multiplicity of the diffracting crystal planes. The grain size of an unknown sample can then be determined by a quantitative analysis of the diffraction ring.

DETAILED DESCRIPTION

X-ray diffraction data can be collected using one-dimensional diffraction (1D) profiles and two-dimensional (2D) profiles. One dimensional profiles are measured by rotating the sample and detecting diffracted X-rays with scanning point detectors or linear position-sensitive detectors. Two-dimensional profiles are acquired with two-dimensional, or area, detectors and the resulting data is then processed using two-dimensional image processing and two-dimensional diffraction pattern manipulation and interpretation. The two-dimensional diffraction pattern consists of a plurality of concentric rings.

Figure 1:
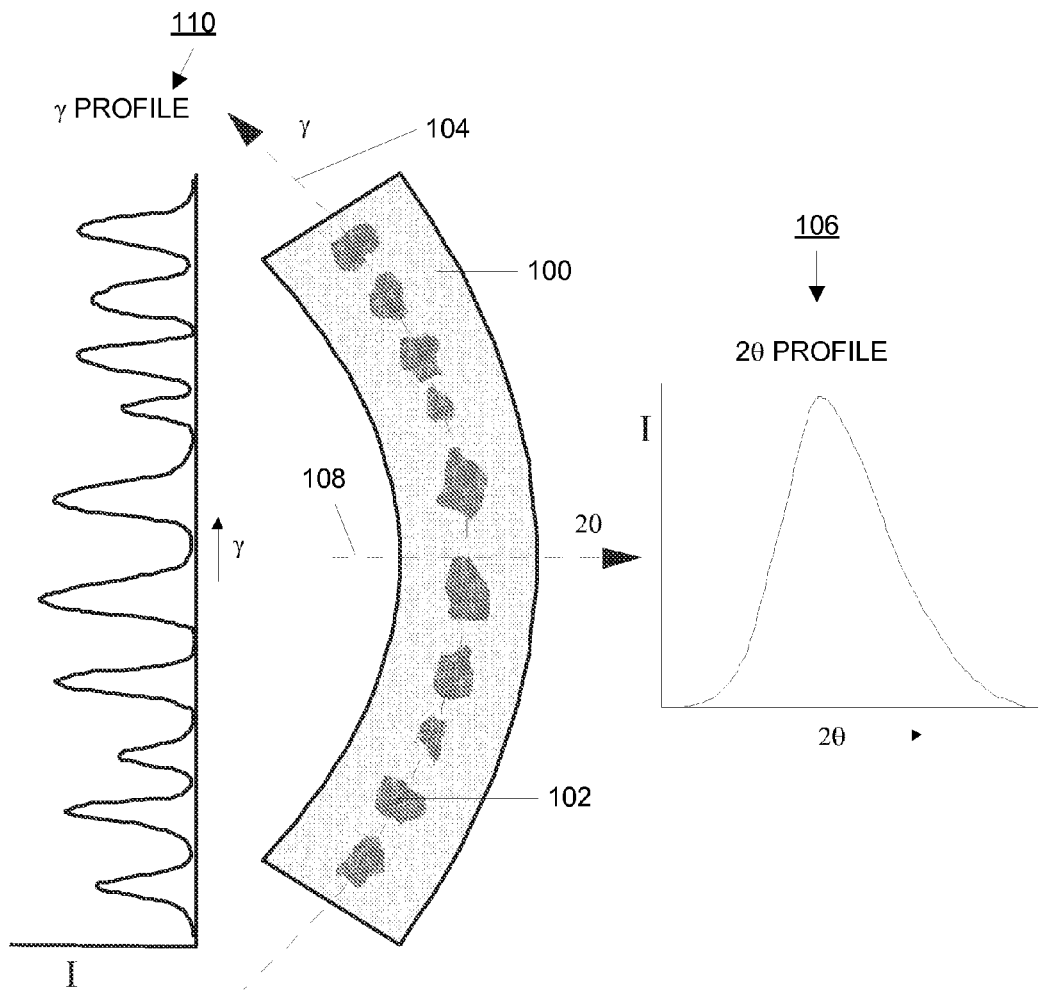
FIG. 1 is a schematic diagram of a two-dimensional X-ray diffraction ring illustrating a comparison of the conventional 2θ profile analysis method and the inventive γ profile analysis method for particle size measurement.

FIG. 1 illustrates a section 100 of a "spotty" two-dimensional diffraction ring pattern produced from a sample with a relatively large crystallite size. Each spot, such as spot 102, corresponds to a crystallite which happens to satisfy the diffraction condition (Bragg Law). It has long been recognized "spotty" diffraction rings are produced from sample with large crystallite size, but no prior art methods have been available to determine the crystallite size from such patterns.

FIG. 1 also illustrates a comparison between the conventional (based on 2θ profile analysis) method for determining particle size and the inventive method (based on γ profile analysis). More specifically, integration of the diffraction pattern 100 in the γ direction as indicated by arrow 104 generates a diffraction profile 106 of intensity (I) vs. 2θ angle. For small particle sizes, this profile can be used to measure the particle size by the conventional 2θ profile analysis discussed above. Diffraction profiles for 2θ profile analysis can also be obtained by a conventional diffractometer with a point or line detector.

Figure 2:
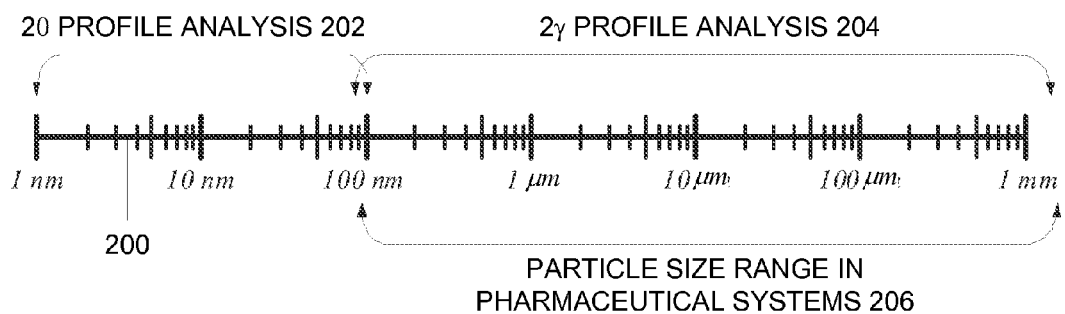
FIG. 2 is a line graph of particle size illustrating the size ranges for which the conventional 2θ profile analysis method is satisfactory and the size ranges for which the inventive γ profile analysis method produces satisfactory results.

The integration of the diffraction pattern 100 in the 2θ direction, indicated by arrow 108, generates a γ profile 110 of intensity (I) vs. angle (γ). In accordance with the principles of the invention, profile 110 can be used to calculate the particle size. The inventive γ profile analysis extends the measurement range of the crystallite size from below 100 nm to several millimeters as shown in FIG. 2 which is a line graph 200 of particle sizes starting from 1 nm at the left and increasing to 1 mm at the right. The conventional line profile analysis based on 2θ profile analysis is suitable for measuring crystallite sizes smaller than 100 nm (1000 Å) as indicated by bracket 202, while the inventive γ-profile analysis is more suitable for larger crystallites from 0.1 μm to a few millimeters depending on the x-ray incident beam size, divergence, sample shape and size, instrument geometry and detector resolution as indicated by bracket 204. This latter size range corresponds to the particle sizes used in most pharmaceutical systems, which are shown as bracket 206.

The inventive γ profile analysis is based on sampling statistics. Sampling statistics believed to be "poor" for other applications are actually preferred for crystallite size determination. The sampling statistics are determined by both the sample structure and instrumentation. For a perfect random powder sample, the number of contributing crystallites for a measured diffraction line can be given by $$N_s = p_{hkl} \cdot \frac{Vf_i}{v_i} \cdot \frac{\Omega}{4\pi} \tag{1}$$

where $p_{hkl}$ is the multiplicity of the diffracting planes, V is the effective sampling volume, $f_i$ is the volume fraction of the crystallites being measured; $f_i=1$ for single phase materials, $v_i$ is the volume of individual crystallites and Ω is the angular window of the instrument in solid angle. The factor $Vf_i/v_i$ is the number of the crystallites being measured within the effective volume. The factor $\Omega/4\pi$ is the ratio of the effective volume satisfying the Bragg condition. The multiplicity factor, $p_{hkl}$, effectively increases the number of crystallites contributing to the integrated intensity from a particular set of (hkl) planes. The volume of individual crystallites, $v_i$ is an average of various crystallite sizes or assumes all crystallites have the same volume.

Figure 3:
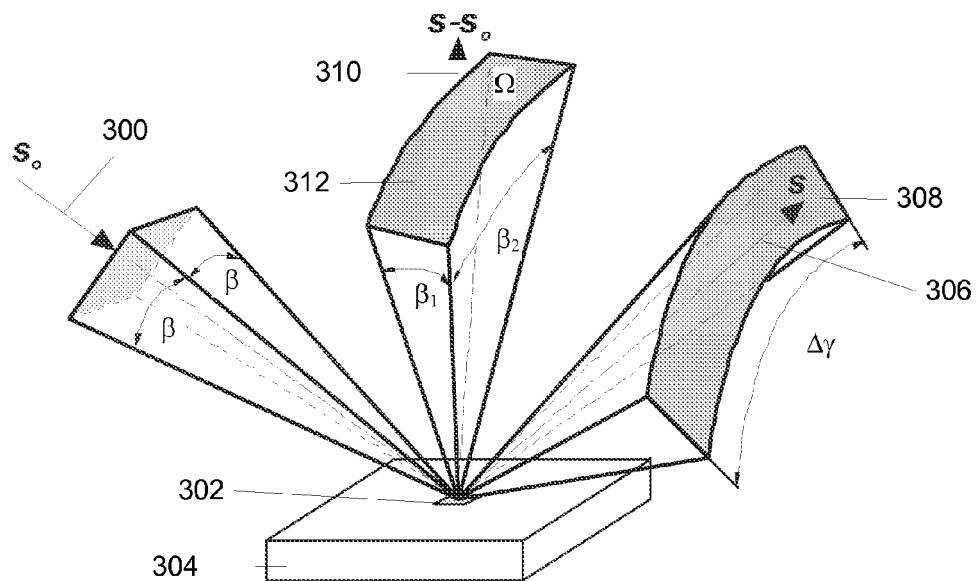
FIG. 3 is a schematic diagram illustrating factors that affect the instrumental window Ω.

Assuming sphere-shaped particles, the term $v_i$ can be replaced by the particle size, $v_i=\pi d_i^3/6$, where $d_i$ is the diameter of the crystallite particles. The combination of the effective sampling volume and the angular window makes up the instrumental window, which determines the total volume of polycrystalline material making a contribution to the diffraction pattern. In two-dimensional x-ray diffraction, the instrumental window is not only determined by the incident beam size and divergence, but also by the γ angular range (the detection area and sample-to-detector distance). FIG. 3 illustrates the factors that determine the instrumental window. $S_o$ (300) is a vector representing the an X-ray beam with divergence β that is incident on a sample 302 held on a sample holder 304. Vector S (306) represents the diffracted beam as seen by the detector (not shown in FIG. 3) which is a section of the ring-shaped two-dimensional diffraction pattern 308. Vector S-S$_o$ (310) represents the diffraction vector and the instrumental window Ω (312). As shown in FIG. 3, the instrumental window Ω is given by $$\Omega = \beta_1 \beta_2 = 2\beta \arcsin[\cos\theta \sin(\Delta\gamma/2)] \tag{2}$$

where $\beta_1$ is the instrument angular window in the 2θ direction and $\beta_2$ is the instrumental window in the γ direction, or the diffraction vector angular range corresponding to the azimuthal angular range Δγ. Neglecting the instrumental broadening effect of the detector, the instrument window in the 2θ direction can be given by the divergence of the incident angle ($\beta_1=\beta$). Particle broadening may also affect the above relation, but since γ-profile analysis deals with relative large crystallites, particle broadening is negligible.

The diffraction data for γ profile analysis can be collected with a two-dimensional x-ray diffraction (XRD$^2$) system operating in either transmission mode or reflection mode. In reflection mode, if the data is collected at the x-ray incident angle ω=θ the effective sampling volume can be approximated by $$V = \frac{A_0}{2\mu} = \frac{\pi b^2}{8\mu} \tag{3}$$

where $A_o$ is the cross section of the incident x-ray beam and μ is the linear absorption coefficient. In two-dimensional X-ray diffraction, a round point beam is typically used, so the beam cross section $A_o = \frac{1}{4}\pi b^2$ and b is the size of the incident beam in diameter. Inserting equations (3) and (2) into equation (1), the crystallite volume for the i$^{th}$ phase is calculated as $$v_i = \frac{p_{hkl} f_i A_0 \beta \arcsin[\cos\theta \sin(\Delta\gamma/2)]}{4\pi \mu N_s} \tag{4}$$

where $N_s$ is the number of crystallites contributing to the diffraction pattern within the instrumental window and effective sampling volume. Given a material with single phase, $f_i=1$, and replacing $v_i$ by the diameter of the crystallite particles d (v=πd$^3$/6), the crystallite size is then given by $$d = \left\{ \frac{3 p_{hkl} A_0 \beta \arcsin[\cos\theta \sin(\Delta\gamma/2)]}{2\pi^2 \mu N_s} \right\}^{\frac{1}{3}} \tag{5}$$

Introducing a scaling factor covering all the numeric constants, incident beam divergence and calibration factor for the instrument, the equation for the crystallite size measurement in reflection mode is:

$$d = k \left\{ \frac{p_{hkl} b^2 \arcsin[\cos\theta \sin(\Delta\gamma/2)]}{2\mu N_s} \right\}^{\frac{1}{3}} \tag{6}$$

where $$k = \left(\frac{3\beta}{4\pi}\right)^{\frac{1}{3}}$$

if the instrumental broadening in 2θ direction is known. Alternatively, if the instrumental broadening in 2θ direction is not known, k may be treated as a calibration factor which can be determined from the 2D diffraction pattern of a known standard. Since only a limited number of spots along the diffraction ring can be resolved, it is apparent from equation (6) that a smaller x-ray beam size and low multiplicity peak should be used if a smaller crystallite size is to be determined.

If the two-dimensional X-ray diffraction system is operated in transmission mode with the incident beam perpendicular to the sample surface, the effective sampling volume is given by:

$$V = A_0 t \exp(-\mu t) = \frac{1}{4}\pi b^2 t \exp(-\mu t) \quad (7)$$

where t is the thickness of the sample. The effective sampling volume reaches a maximum for transmission mode diffraction when $t=1/\mu$.

It can be observed from the above equations that the effective sampling volume is proportional to the beam cross section area and is lower for materials with higher linear absorption coefficients. The effective sampling volume given by the above two equations (3) and (7) takes into account the sampling statistics and their effect on the scattering intensities. For crystallite size analysis, sample absorption has a different effect on the sampling volume in reflection and transmission modes. In reflection mode, the linear absorption coefficient determines how fast the incident beam is attenuated within the sample, but there is no clear cutoff for the penetration depth. Therefore, the effective sampling volume has to be used. In transmission mode with the incident beam perpendicular to the sample surface, the linear absorption coefficient affects the relative scattering intensity (counting statistics), but not the actual sampling volume. In other words, all the sample volume within the beam path contributes to the diffraction. Therefore, it is reasonable to ignore the absorption effect $\exp(\mu t)$ for crystallite size analysis as long as the sample is thin enough for transmission mode diffraction. The actual sampling volume can then be given simply by:

$$A_0 t = \frac{1}{4}\pi b^2 t \quad (8)$$

In the above equations, the incident beam size should be measured at the sample location (instrument center). Introducing equations (8) and (2) into (1), we obtain the crystallite volume for the $i^{th}$ phase as $$v_i = \frac{p_{hkl} f_i A_0 t \beta \arcsin[\cos\theta \sin(\Delta\gamma/2)]}{2\pi N_s} \quad (9)$$

Considering a material with a single phase, $f_i=1$, and replacing $v_i$ by the diameter of the crystallite particles d ($v=\pi d^3/6$), the crystallite size is then given by:

$$d = \left\{\frac{3p_{hkl}b^2 t\beta \arcsin[\cos\theta\sin(\Delta\gamma/2)]}{4\pi N_s}\right\}^{\frac{1}{3}} \quad (10)$$

Introducing a scaling factor k to cover all the numeric constants, incident beam divergence and the calibration factor for the instrument, we obtain an equation for crystallite size measurement in transmission mode:

$$d = k\left\{\frac{p_{hkl_i}b^2 t\arcsin[\cos\theta\sin(\Delta\gamma/2)]}{N_s}\right\}^{\frac{1}{3}} \quad (11)$$

where $$k = \left(\frac{3\beta}{4\pi}\right)^{\frac{1}{3}}$$

if the instrumental broadening in the 2θ direction is known. k may also be treated as a calibration factor which can be determined from the 2D diffraction pattern of a known standard. By using the relationships given by either equation (6) or equation (11), crystallite size analysis becomes a task of resolving the number of crystallites measured in a section of diffraction ring.

One method for determining the number of crystallites is to count the number of intersections of the γ-profile with a threshold line. This line can be a horizontal straight line based on the average intensity or background. For example, a straight horizontal line representing the average intensity of the γ-profile can be used. Every two intersections of γ-profile with this horizontal line represents a crystallite. In order to cancel out the effects of preferred orientation and other material and instrumental factors on the overall intensity fluctuation along the γ-profile, a trend line can be used as a threshold line. The threshold line can be set at a series level of overall intensities, for instance from 10% average intensity to 190% average intensity with 10% steps. In this way, the crystallite size distribution can be analyzed, assuming the spot intensity is a function of the crystal size.

Figure 4:
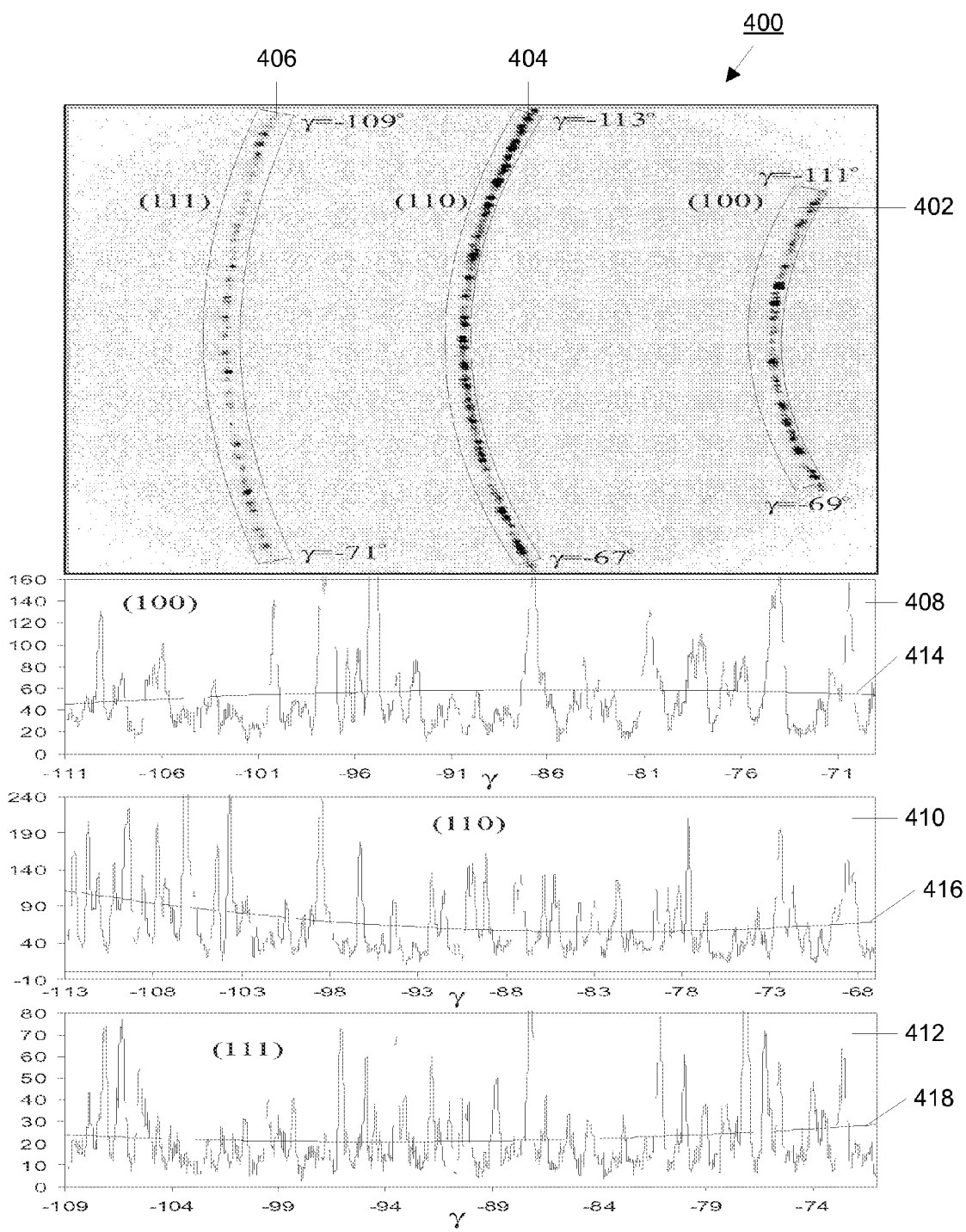
FIG. 4 shows a frame collected from an SRM660a standard sample with a two-dimensional X-ray diffraction system with three rings from the (100), (110) and (111) planes and three γ profiles generated from the three rings.

FIG. 4 illustrates diffraction patterns and γ-profiles used in a method for calibrating an instrument to determine the scaling factor k. Pattern 400 is a frame collected from an SRM660a (LaB$_6$) sample with a two-dimensional X-ray diffraction system (a D8 DISCOVER™ system operating with GADDS™ CST software manufactured by Bruker AXS Inc., Madison, Wis.) for combinatorial screening in transmission mode with Cu—K$_\alpha$ X-rays. The 2D detector (a Hi-Star™ model 2D detector manufactured by Bruker AXS) is set at 23.75 cm from the instrument center. The beam (collimator pinhole) size b is 200 μm. From equation (11), it can be seen that an accurate sample thickness value (t) is required for system calibration. One way to determine the sample thickness value is to calculate the sample thickness from the measured transmission coefficient. This is especially practical for packed loose powder samples. Based on the calculated linear absorption coefficient of 1138 cm$^{-1}$ (0.1138 μm$^{-1}$) and the measured transmission of 0.45 for the LaB$_6$ sample, the sample thickness t is calculated at 7.0 μm. A scanning electron microscope analysis on the SRM660a sample indicated that the particles of LaB$_6$ consist of aggregates of crystallites in the size range from 2μ to 5 μm. From this range, an average crystallite size d is determined as 3.5 μm.

Three rings 402, 404 and 406 respectively, from the (100), (110) and (111) planes are observed in the resulting two-dimensional X-ray diffraction pattern 400. The 2θ-integrated plots (γ-profiles 408, 410 and 412, respectively) for the rings are shown under the diffraction pattern 400. In FIG. 4, a $2^{nd}$ order polynomial trend line of the intensities is fitted to each γ-profile (trend lines 414, 416 and 418, respectively). The number of crystallites is counted as half of the number of intersections between the γ-profile and the trend line. Since in this case the SRM660a (LaB$_6$) sample has a known average crystallite size, all three diffraction rings are used to calibrate the instrument for crystallite size determination. The calibration results with the LaB$_6$ standard are listed in Table 1.

TABLE 1

| (hkl) | $P_{hkl}$ | 2θ | Δω | $N_s$ | k |
|---|---|---|---|---|---|
| (100) | 6 | 21.36 | 38 | 23 | 0.1217 |
| (110) | 12 | 30.38 | 46 | 41 | 0.1106 |
| (111) | 8 | 37.44 | 42 | 38 | 0.1281 |

Thus, the average scaling factor k is 0.12 in this calibration. After this calibration, the X-ray diffraction system can be used to measure the crystallite size of unknown materials if the data can be collected under approximately the same conditions. It is always necessary to calibrate the X-ray diffraction system with a known standard, preferably with a geometry and a crystallite size comparable to the unknown sample. For reflection mode, it is critical to have a standard with a comparable linear absorption coefficient so as to have similar x-ray penetration.

The trend line from a certain percentage of the intensities may also be used to count the intersections. The lower the percentage is, the more sensitive the analysis is to weak spots, but the analysis will be more affected by background noise. The most important thing is to be consistent with the threshold line for the standard and unknown samples. The γ-resolution on crystal spots can be improved by using a long sample-to-detector distance. Reducing the x-ray beam size, beam divergence and sample thickness can reduce the number of spots along the γ-profile so as to reduce the demand for γ-resolution. Using a diffraction line with low multiplicity also reduces the demand for γ-resolution. In cases where too few diffraction spots can be observed in the diffraction ring, a large beam size or sample oscillation (by rotation or translation) may improve the sampling statistics. However, the system should be calibrated in the same condition with a known sample having comparable crystallite size.

The linear absorption coefficient has been built into the equation for reflection mode and the sample thickness has been built in the equation for transmission mode. In principle, the linear absorption coefficient or the thickness of the calibration standard sample does not have to match the sample to be measured. The extent of the effect of discrepancies in the linear absorption coefficient or in the thickness on the γ-profile has not been rigorously studied, but in order to reduce the geometry error or any unknown factors caused by such a discrepancy, the standard sample material may be diluted by light and amorphous materials in order to produce a standard sample with various linear absorption coefficients or matching thicknesses. For example, a diluted LaB6 sample with various linear absorption coefficients or matching thickness for profile analysis can be made by mixing the LaB6 with different amounts of starch.

For samples with very large crystallite size relative to the X-ray beam size, the number of spots on the diffraction ring may be too few to allow a reliable count. In this case, the effective sample volume can be increased to cover more crystallites by scanning the X-ray beam over a predetermined area of the sample or by collecting a diffraction frame at multiple target areas of the sample. In the multiple target method, one diffraction frame is collected by accumulating the diffracted X-rays at all of the multiple targets. Alternatively, multiple frames can be collected with one frame on each target, and then all frames added to produce one frame. With this method there is no need to perform a calibration on each of the multiple targets. Instead, the scaling factor for the multiple targets can be calculated from the scaling factor for a single target by the following equation:

$$k_n = n^{1/3} k \quad (12)$$

where k is the scaling factor for a single target, n is the number of targets in the multiple target strategy, and $k_n$ is the scaling factor used for the calculation of the crystallite size from the γ profile obtained from the multiple targets. The measurement range of crystallite sizes can be extended by simply increasing the number of targets in the measurement.

Figure 5:
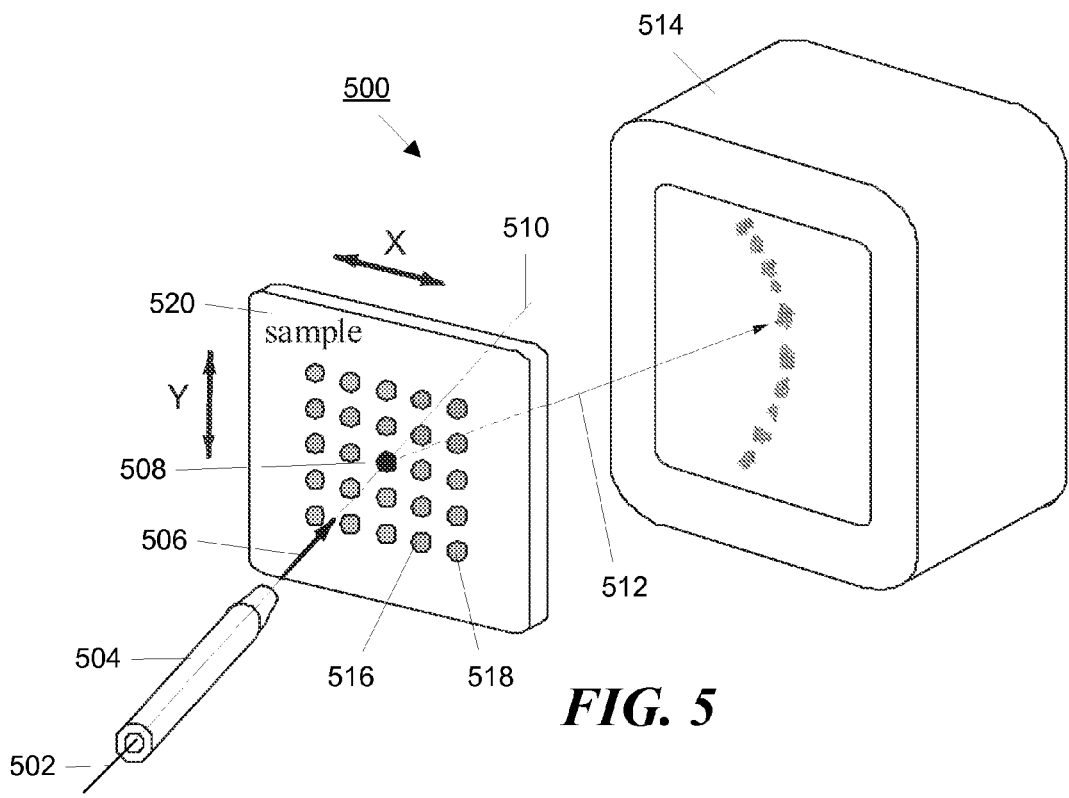
FIG. 5 is a perspective schematic diagram that illustrates a multiple target method with an X-ray diffraction system operating in transmission mode that can be used to determine crystallite numbers in samples with very large crystallite size.

FIG. 5 illustrates the multiple target method with an X-ray diffraction system 500 operating in transmission mode. The X-ray beam 502 passes through the collimator 504 so that the beam size is determined by the collimator 504. The collimated X-ray beam 506 then impinges on a sample spot 508 and is transmitted through the sample 508 as beam 510. Diffracted X-rays 512 reach the 2D detector 514 where diffraction spots from some crystallites can be recorded. If the crystallite size is very large, few or no diffraction spots may be generated from the single target 508. However, in accordance with the method, an array of sample targets, 516, 518, etc. are selected on the sample plate. The sample mounted on a sample holder 520 can be translated in the X and Y directions under control of a stepper motor (not shown). The X and Y travel of the sample holder 520 brings each sample target into the X-ray beam 506 sequentially so the recorded diffraction ring contains possible diffraction spots of all targets. Assuming the scaling factor is k for a single spot and a total of 25 targets are measured by X and Y translation, the scaling factor k in equation (11) is given by equation (12) as:

$$k_n = 25^{1/3} k = 2.924 k$$

The determination of the calibration factor for a system operating in reflection mode follows the same working principle.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for measuring crystallite size of a sample with a two-dimensional X-ray diffraction system having an area X-ray detector, comprising:
    (a) obtaining a two-dimensional diffraction pattern having a diffraction ring with an intensity distribution from the sample with the detector;
    (b) integrating the intensity distribution of a section of the diffraction ring along a 2θ direction to produce a γ profile of intensity versus azimuth angle γ; and
    (c) determining the crystallite size from the γ profile.

2. The method of claim 1 wherein step (c) comprises determining a number of crystallites in the diffraction ring section.

3. The method of claim 2 wherein step (c) further comprises obtaining a scaling factor for the two-dimensional X-ray diffraction system by obtaining a diffraction ring pattern with an intensity distribution from a standard sample having a known crystallite size, integrating the intensity distribution of a section of the diffraction ring along a 2θ direction to produce a γ profile and using the γ profile and the known crystallite size to determine the scaling factor.

4. The method of claim 2 wherein step (c) comprises using a relationship between the number of crystallites in the diffraction ring section and the crystallite size to determine the crystallite size.

5. The method of claim 4 wherein the two-dimensional X-ray diffraction system has an X-ray incident beam and operates in reflection mode and the relationship is $$d = k\left\{\frac{p_{hkl}b^2\arcsin[\cos\theta\sin(\Delta\gamma/2)]}{2\mu N_s}\right\}^{\frac{1}{3}}$$

where d is the crystallite size, k is a scaling factor, $p_{hkl}$ is a multiplicity factor that increases the number of crystallites contributing to the integrated intensity from a particular set of (hkl) planes, b is a size of the X-ray incident beam in diameter, θ is an incident angle of the X-ray beam, Δγ is the azimuth angle spanned by the diffraction ring section, μ is a linear absorption coefficient and $N_s$ is the number of crystallites in the diffraction ring section.

6. The method of claim 5 wherein $$k = \left(\frac{3\beta}{4\pi}\right)^{\frac{1}{3}}$$

when instrumental broadening in 2θ direction (β) caused by the two-dimensional X-ray diffraction system is known.

7. The method of claim 5 wherein k is determined by obtaining a diffraction ring pattern with an intensity distribution from a standard sample having a known crystallite size, integrating the intensity distribution of a section of the diffraction ring along a 2θ direction to produce a γ profile and using the γ profile and the known crystallite size to determine the scaling factor.

8. The method of claim 4 wherein the two-dimensional X-ray diffraction system has an X-ray incident beam and operates in transmission mode and the relationship is $$d = k\left\{\frac{p_{hkl_i}b^2 t\arcsin[\cos\theta\sin(\Delta\gamma/2)]}{N_s}\right\}^{\frac{1}{3}}$$

where d is the crystallite size, k is a scaling factor, $p_{hkl}$ is a multiplicity factor that increases the number of crystallites contributing to the integrated intensity from a particular set of (hkl) planes, b is a size of the X-ray incident beam in diameter, t is a sample thickness value θ is an incident angle of the X-ray beam, Δγ is the azimuth angle spanned by the diffraction ring section and $N_s$ is the number of crystallites in the diffraction ring section.

9. The method of claim 8 wherein $$k = \left(\frac{3\beta}{4\pi}\right)^{\frac{1}{3}}$$

when instrumental broadening in 2θ direction (β) caused by the two-dimensional X-ray diffraction system is known.

10. The method of claim 8 wherein k is determined by obtaining a diffraction ring pattern with an intensity distribution from a standard sample having a known crystallite size, integrating the intensity distribution of a section of the diffraction ring along a 2θ direction to produce a γ profile and using the γ profile and the known crystallite size to determine the scaling factor.

11. The method of claim 2 wherein the number of crystallites in the diffraction ring section is determined by counting intersections of the γ-profile with a threshold line.

12. The method of claim 11 wherein the threshold line comprises a straight line representing an average intensity of the γ-profile.

13. The method of claim 11 wherein the threshold line comprises a trend line.

14. The method of claim 13 wherein the trend line is a second order polynomial trend line.

15. The method of claim 11 wherein the threshold line comprises a stepped line with each step representing a percentage level of overall intensity.

16. The method of claim 1 wherein step (a) comprises obtaining a two-dimensional diffraction pattern by scanning over an area on the sample.

17. The method of claim 1 wherein step (a) comprises obtaining a two-dimensional diffraction pattern by collecting diffraction data at a plurality of target areas on the sample.

18. The method of claim 17 wherein the diffraction data is collected by accumulating diffracted X-rays at all of the plurality of target areas.

19. The method of claim 17 wherein the diffraction data is collected by obtaining a diffraction pattern from each area of the plurality of target areas, and adding the diffraction patterns together to produce one diffraction pattern.

20. The method of claim 17 wherein an overall scaling factor used in a calculation of crystallite size from a γ profile is calculated by determining a scaling factor at a single target area and using the relationship $k_n = n^{1/3}k$ where k is the scaling factor for the single target area, n is the number of target areas on the sample, and $k_n$ is the overall scaling factor.

* * * * *